US012617014B2

(12) United States Patent
Katti et al.

(10) Patent No.: US 12,617,014 B2
(45) Date of Patent: May 5, 2026

(54) AU, AG AND RICH PHYTOCHEMICAL PAYLOAD NANOMATERIALS, ANTIVIRAL/ANTIBACTERIAL PRODUCTS AND SYNTHESIS METHODS

(71) Applicant: THE CURATORS OF THE UNIVERSITY OF MISSOURI, Columbia, MO (US)

(72) Inventors: Kattesh V. Katti, Columbia, MO (US); Kavita K. Katti, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 272 days.

(21) Appl. No.: 18/558,576

(22) PCT Filed: May 10, 2022

(86) PCT No.: PCT/US2022/028472
§ 371 (c)(1),
(2) Date: Nov. 2, 2023

(87) PCT Pub. No.: WO2022/245578
PCT Pub. Date: Nov. 24, 2022

(65) Prior Publication Data
US 2025/0281637 A1 Sep. 11, 2025

Related U.S. Application Data

(60) Provisional application No. 63/297,937, filed on Jan. 10, 2022, provisional application No. 63/189,420, filed on May 17, 2021.

(51) Int. Cl.
*B22F 1/102* (2022.01)
*A61K 36/18* (2006.01)
*A61K 47/69* (2017.01)
*A61P 31/14* (2006.01)
*A61P 35/00* (2006.01)
*B82Y 5/00* (2011.01)

(52) U.S. Cl.
CPC .............. *B22F 1/102* (2022.01); *A61K 36/18* (2013.01); *A61K 47/6923* (2017.08); *A61K 47/6929* (2017.08); *A61P 31/14* (2018.01); *A61P 35/00* (2018.01); *A61K 2236/15* (2013.01); *A61K 2236/331* (2013.01); *A61K 2236/37* (2013.01); *A61K 2236/53* (2013.01); *B82Y 5/00* (2013.01)

(58) Field of Classification Search
None
See application file for complete search history.

(56) References Cited

U.S. PATENT DOCUMENTS

2007/0161818 A1 7/2007 Li et al.
2019/0105261 A1 4/2019 Waugh et al.

FOREIGN PATENT DOCUMENTS

PL 235907 B1 * 11/2020 ................ B22F 9/24

OTHER PUBLICATIONS

Anonymous, CAS Scifinder entry for Quercetin (RN=117-39-5), accessed in CAS SciFinder on Sep. 27, 2025.*
Anonymous, CAS SciFinder entry for Sweroside (RN=14215-86-2), accessed in CAS SciFinder on Sep. 27, 2025.*
Anonymous, CAS SciFinder entry for Shikimic acid (RN=138-59-0), accessed in CAS SciFinder on Sep. 27, 2025.*
Ayrilmis et al., Journal of Polymers and the Environment (2021), 29:2409-2420.*
Meka et al., Nanoscale (2019), 11, pp. 7931-7943.*
Abouaitah, et al., "Virucidal Action Against Avian Influenza HSN I Virus and Immunomodulatory Effects of Nanoformulations Consisting of Mesoporous Silica Nanoparticles Loaded with Natural Prodrugs", International Journal of Nanomedicine, 2020, vol. 15, pp. 5181-5202.
Banach, et al., "Proecological method for the preparation of metal nanoparticles", Journal of Cleaner Production, 2017, vol. 141, pp. 1030-1039.
Bilgili, et al., "Liquidambar Orientals Mill. Leaf Aqueous Extract for the Synthesis of Silver Nanoparticles and Immobilization on Textile Fabrics for Biomenical Applications", Tekstil ve Konfeksiyon, 2016, vol. 26(4), pp. 421-429.
Lipsa, et al., "Evaluation of the Antifungal Activity of Gold-Chitosan and Carbon Nanoparticles on Fusarium oxysporum", Agronomy, 2020, vol. 10, 1143, pp. 1-11.
Rónavári, et al., "Biological activity of green-synthesized silver nanoparticles depends on the applied natural extracts: a comprehensive study", International Journal of Nanomedicine, 2017, vol. 12, pp. 871-883.
Rónavári, et al., "Biosynthesized silver and gold nanoparticles are potent antimycotics against opportunistic pathogenic yeasts and dermatophytes", International Journal of Nanomedicine, 2018, vol. 13, pp. 695-703.
International Search Report from the corresponding International Patent Application No. PCT/US2022/028472, dated Aug. 9, 2022.

* cited by examiner

*Primary Examiner* — Brian J Davis

(74) *Attorney, Agent, or Firm* — Greer, Burns & Crain, Ltd.; Steven P. Fallon

(57) ABSTRACT

A nanomaterial is gold or silver nanoparticle having a nanoparticle surface that consists of one or more of the following extracts from sweet gum leaves: shikimic acid, sweet gum leaf family of Catechins, sweet gum leaf family of Quercetin, Sweroside, Afzelechin, p-Coumaric Acid, Epi-afzelechin Trimethyl Ether, Myricetin, Naringenin, Phloretin, Procyanidin B1 and related polyphenols, flavonoids and alkaloids. An antiviral/antibacterial agent includes sweet gum mediated silver nanoparticles having a core size and in a concentration having efficacy as an antiviral/antibacterial exceeding a 3 log 10 reduction in viral titer.

11 Claims, No Drawings

AU, AG AND RICH PHYTOCHEMICAL PAYLOAD NANOMATERIALS, ANTIVIRAL/ANTIBACTERIAL PRODUCTS AND SYNTHESIS METHODS

PRIORITY CLAIM AND REFERENCE TO RELATED APPLICATION

The application claims priority under 35 U.S.C. § 119 and all applicable statutes and treaties from prior U.S. provisional application Ser. No. 63/297,937, which was filed Jan. 10, 2022, and from U.S. provisional application Ser. No. 63/189,420, which was filed May 17, 2021.

TECHNICAL FIELD

A field of the invention is composite nanomaterials. Example applications of the invention include biomedical applications such as disease treatment and disease detection. Another field of the invention is antiviral/antibacterial products and treatments. Another field of the invention is nanotechnology

BACKGROUND

Antiviral agents are important to protect human civilization from pandemics. Effective antivirals can provide an important defense to the spread of viral based pandemics, including the family of SARS-COV-2 (which causes COVID-19) and influenza viruses (which causes the seasonal flu) viruses.

Bulk silver itself has been recognized and used over time in antifungal, antibacterial and anti-viral applications. Bulk silver itself is not suitable as an antiviral/antibacterial agent.

Chitosan-stabilized gold nanoparticles have been investigated for their antifungal properties against the pathogen *Fusarium oxysporum*. Lipsa et al., valuation of the Antifungal Activity of Gold-Chitosan and Carbon Nanoparticles on *Fusarium oxysporum*," Agronomy 2020, 10, 1143. Antifungal properties were attributed to the efficacy of the chitosan and how it was enhanced via the combination of gold-chitosan nanoparticles. The targeted application is to control fungus in agricultural fields. As noted, the properties of the particles are particular to the coating and reduction agent.

Gold and silver nanoparticles were fabricated via a *P. rhodozyma* cell-free extract. Rónavári et al, "Biosynthesized silver and gold nanoparticles are potent antimycotics against opportunistic pathogenic yeasts and dermatophytes," International Journal of Nanomedicine 2018:13, 695-703. The described testing reported that the particles were effective against specific mycois-causing fungal species, except for *C. tropicalis*.

AgNPs obtained by chemical reduction using coffee and green tea extracts were reported to have antimicrobial efficiency. Rónavári A, Kovacs D, Igaz N, et al. Biological activity of green-synthesized silver nanoparticles depends on the applied natural extracts: a comprehensive study. Int J Nanomedicine. 2017; 12:871-883. As indicated, specific synthesis routes provide unpredictable biological activities.

SUMMARY OF THE INVENTION

A preferred embodiment provides a nanomaterial of gold or silver nanoparticle having a nanoparticle surface that consists of one or more of the following extracts from sweet gum leaves: shikimic acid, sweet gum leaf family of Catechins, sweet gum leaf family of Quercetin Sweroside, Afzelechin, p-Coumaric Acid, Epiafzelechin Trimethyl Ether, Myricetin, Naringenin, Phloretin, Procyanidin B1 and related polyphenols, flavonoids and alkaloids. An antiviral/antibacterial agent includes sweet gum mediated silver nanoparticles having a core size and in a concentration having efficacy as an antiviral exceeding a 3 log 10 reduction in viral titer.

DETAILED DESCRIPTION OF THE PREFERRED EMBODIMENTS

Preferred embodiments provide silver nanoparticle antiviral/antibacterial products and pharmaceuticals. Products include antiviral/antibacterial sprays, antiviral/antibacterial wipes, and antiviral/antibacterial cotton textiles. A pharmaceutical includes sweet gum plant phytochemical-mediated silver nanoparticles in an oral consumption carrier for use as a pharmaceutical to treat viruses, including the family of SARS-COV-2 (which causes COVID-19) and influenza viruses (which causes the seasonal flu). Preferred silver nanoparticle antiviral/antibacterial agents of the invention demonstrated a 3.50 Log 10 reduction in viral titer (99.97%) at a contact time of 1 minute and a corresponding 3.75 Log 10 reduction in viral titer (99.98%) at a contact time of 5 minutes, as compared to the titer of the corresponding Plate Recovery Control. Preferred embodiments also include green and zero carbon fabrication methods of silver nanoparticle antiviral/antibacterial agents using sweet gum plant mediated formation.

Preferred silver nanoparticles are encapsulated with antiviral/antibacterial phytochemicals. The construct provides the for neutralizing deadly COVID-19 and related viruses by penetrating the viral envelope composed of a lipid bilayer membrane, in COVID-19, in which the glycoprotein spikes are anchored encloses the nucleocapsids. The neutralization of the virus can occur via dual actions of the antiviral/antibacterial silver nanoparticles as well as the cargo of antiviral/antibacterial phytochemicals that encapsulate surface area of the nanoparticles.

Preferred multicomponent nanomaterials combine physical and biological properties of multiple materials within a single nanoconstruct. Multicomponent nanomaterials provide unique opportunities to combine properties offered separately into a single nanoconstruct. These opportunities can expand applications of a nanomaterials, such as providing simultaneous detection and treatment of various human diseases. Combining multiple components within a single nanomaterial poses significant synthesis challenges. Many efforts to combine different materials into a single nanomaterial result in the loss of one or more desired properties of the individual materials, while preferred embodiments provide tailored and desired properties.

Sweet gum tree, native plant found abundantly in Southeastern United States, exudes a highly valuable phytochemical called as Shikimic Acid (SA) in its leaves, bark and in its sweetgum fruit. The chemical structure as shown below comprises of 3,4,5-trihydroxy-1-cyclohexene-1-carboxylic acid.

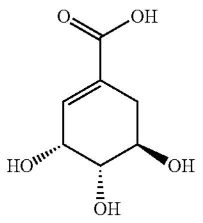 [SMILES: O=C(O)C1=C[C@@H](O)[C@@H](O)[C@H](O)C1]

This compound has found many medical applications as a precursor for the development of antibiotic, antiviral/antibacterial, anti-cancer and immune boosting agents. However, the utility of shikimic acid in its native state, directly from the leaves of Sweet gum tree, in the formulation of antibiotic, antiviral/antibacterial, anti-cancer, immune boosting and related biopharmaceuticals and nutraceuticals has remained largely unexplored. Extracts of phytochemicals, including shikimic acid, directly from plants fail to exhibit optimum bioavailability when administered in vivo in humans and animals. Enzymatic degradation of phytochemicals inside the human body contributes toward the limited bioavailability of shikimic acid.

Preferred methods can embedding shikimic acid on the backbone of Gold or Silver Nanoparticles in order to create multitudes of signatures of the bioactive phytochemical (shikimic acid and other phytochemicals present in sweet gum extract) to make them bioavailable under complex conditions that prevail under in vivo profiles in the human body. In preferred methods, gold nanoparticles are synthesized through direct reduction using electrons present in shikimic acid and cocktail of phytochemicals present in sweet gum extract—without the use of any external toxic chemical reducing agent. The shikimic acid encapsulated gold nanoparticles can provide antibiotic, antiviral/antibacterial, anti-cancer, immune boosting and related biopharmaceuticals and nutraceuticals efficacy.

Preferred embodiments provide methods for encapsulating the following phytochemicals, interconnected through hydrogen bonds, and all bonding onto gold nanoparticulate surface. Preferred nanomaterials provide a gold or silver nanoparticle surface that consists of varying amounts of the following cocktail of phytochemicals beneficial for human/animal health and hygiene: shikimic acid, family of Catechins, family of Quercetin, Sweroside, Afzelechin, p-Coumaric Acid, Epiafzelechin Trimethyl Ether, Myricetin, Naringenin, Phloretin, Procyanidin B1 and a host of related polyphenols, flavonoids and alkaloids.

Preferred embodiments are illustrated through experiments. Artisans will appreciate broader aspects of the invention from the discussion of the experiments.

Synthesis of Sweetgum (*Liquidambar styraciflua*) conjugated gold nanoparticles.

Preparation of phytoextract: Sweet gum Plant leaves were washed with doubly deionized (DI) water and chopped into small pieces. In a conical flask, 4.2 gm chopped leaves were added in 100 ml of DI water. The reaction mixture was heated at 100° C. for 15-20 min on magnetic stirrer. Phytoextract solution was cooled to room temperature (25° C.) and filtered using Whatman filter paper. The phytoextract solution was used for the production of gold nanoparticles.

Estimation of Shikimic Acid in the aqueous extracts of Sweet gum Plant leaves. We have estimated the amount of Shikimic Acid in the aqueous extracts of Sweet gum Plant leaves using both the Gas chromatography-mass spectrometry (GC-MS) and Liquid chromatography-mass spectrometry (LC-MS). Both these techniques inferred the presence of substantial quantities of Shikimic Acid (along with cocktail of other useful phytochemicals as discussed below) in the aqueous extracts of Sweet gum Plant leaves.

Sweet gum leaves extracts in the production of phytochemical cocktail on Gold Nanoparticles Surface: Our detailed LCMS and GCMS analysis of aqueous extracts from sweet gum leaves has identified numerous highly beneficial phytochemicals that are including in coatings of present gold nanoparticles. Gold nanoparticles (as well as Silver nanoparticles) produced by reduction from the sweet gum extracts carry a rich phytochemical payload. The payload consists of shikimic acid, the sweet gum leaf family of Catechins, the sweet gum leaf family of Quercetin, Sweroside, Afzelechin, p-Coumaric Acid, Epiafzelechin Trimethyl Ether, Myricetin, Naringenin, Phloretin, Procyanidin B1 and related polyphenols, flavonoids and alkaloids.

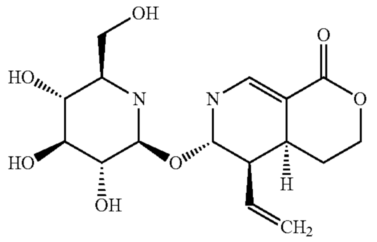

Sweroside

Sweroside possesses strong hepatoprotective effect. Sweroside also has shown a promising anti-osteoporotic effect on the human MG-63 cells and rat osteoblasts.

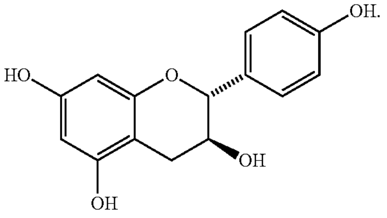

Afzelechin is a flavan-3-ol, a type of flavonoid

Afzelechin exhibits antioxidant and antityrosinase activities. This polyphenol has also shown aphrodisiac, antihypertensive, anticancer, antioxidant, hepatoprotective, gastroprotective, antidiabetic, anthelmintic, antimalarial, anti-inflammatory, analgesic and antimicrobial activities.

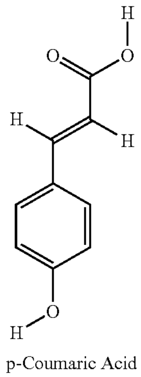 [SMILES: O=C(O)/C=C/c1ccc(O)cc1]

p-Coumaric Acid

Antioxidant activities, in reducing oxidative stress and inflammatory reactions, of p-Coumaric Acid have found applications in the treatment of rheumatoid arthritis (RA). Gold particles produced by a method of the invention include p-Coumaric acid (p-CA). This provides the potential for better absorption in plasma for effective suppression of TNF-α and IL-6-which is helpful in the treatment of rheumatoid arthritis (RA)

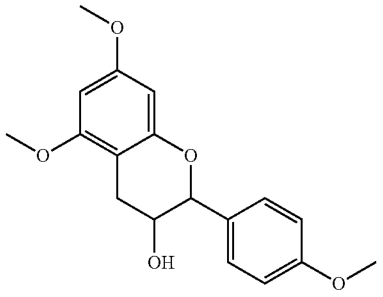

Epiafzelechin Trimethyl Ether

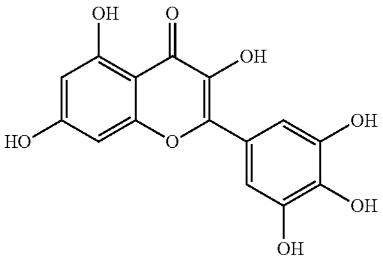

Myricetin

Myricetin is embedded in gold nanoparticles produced by present methods along with Shikimic acid. This combination is vital for the as a nano flavonoid for its nutraceuticals value. Myricetin exhibits a wide range of activities including strong antioxidant, anticancer, antidiabetic and anti-inflammatory activities. It plays a vital role in the central nervous system to protect against diseases such as Parkinson's and Alzheimer's.

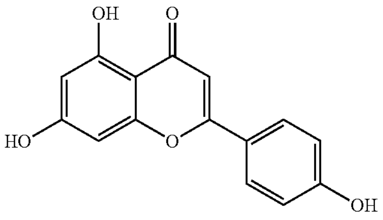

Naringenin

Naringenin is a flavonoid that belongs to flavanones subclass. It is a powerful natural antioxidant displaying antitumor, antiviral, antibacterial, anti-inflammatory, antiadipogenic and cardioprotective effects.

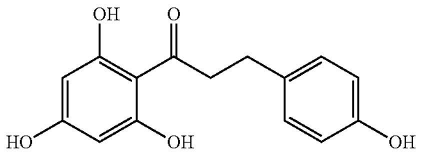

Phloretin

Phloretin, a natural phenolic compound, that exhibits a myriad of activities including antioxidative, anti-inflammatory, anti-microbial, anti-allergic, anticarcinogenic, antithrombotic, and hepatoprotective. It is also involved in the activation of apoptotic associated gene expression and signal transduction in molecular pathways. Incorporation of Phloretin on gold nanoparticles enhances its bioavailability and thus would enhance its therapeutic potential

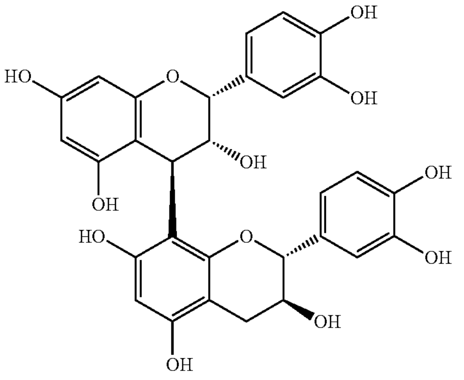

Procyandidn B

Procyanidin B1, also known as ec-(4b,8)-C or endotelon, belongs to the class of organic compounds. Procyanidin have prolific health benefits with applications that include protection against oxidative damage, and anti-diabetic, anti-cholesterol, and anti-platelet functions. Procyanidin B1 is embedded in the coating on gold nanoparticles produced by present methods and can expand the health benefits of proanthocyanidins because nanosized phytochemicals penetrate cellular membranes more effectively.

Payload of Phytochemicals on Gold Nanoparticles Surface: Preferred embodiments provide encapsulating the following phytochemicals interconnected through hydrogen bonds and all bonding onto gold nanoparticulate surface. A nanomaterial of preferred embodiments includes gold nanoparticle having surface that consists of the following cocktail of phytochemicals beneficial for human/animal health and hygiene: shikimic acid, family of Catechins, family of Quercetin, Sweroside, Afzelechin, p-Coumaric Acid, Epiafzelechin Trimethyl Ether, Myricetin, Naringenin, Phloretin, Procyanidin B1 and related polyphenols, flavonoids and alkaloids.

Synthesis. 1 ml of the aqueous phyto extract from sweet gum plant leaves (SGP), as prepared above, was mixed with 5 ml of DI water, and 12 mg of Gum Arabic protein. Gum Arabic is a natural plant derived polysaccharide protein, a dried exudate of acacia trees (family: Leguminosae). Gum Arabic protein has an average molecular weight of 365,000. US FDA considers the Gum Arabic as a safe food additive.

This reaction mixture was heated at 50-60° C. on magnetic stirrer. Once the temperature reached 60° C., gold salt prepared from sodium tetrachloroaurate (100 μL of 0.1 M) was added to the reaction mixture to produce gold nanoparticles (SGP-AuNPs). Generally, the temperature should be 60° C.-100° C., and the temperature level plays role in controlling the size, morphology and overall quality of nanoparticles. The addition of gold salt to the aqueous phyto extract from sweet gum plant leaves resulted in an instant burgundy red coloration—indicating the characteristic Surface Plasmon Resonance (SPR) and the formation of gold nanoparticles (SGP-AuNP) which have been fully characterized as discussed below.

The nanoparticles were characterized by various instrumentation techniques including, UV-Vis spectrophotometry, Zetasizer Nano S90, TEM and ICP-MS. The data summarized in Table 1 provide full details about the ultraviolet absorption spectral details—characteristic of gold nanoparticles, details of hydrodynamic and core metallic sizes. This table also provides details about the zeta potential which is used to infer the invitro stability of nanoparticles. The Gold content in SGP-gold Nanoparticles were measured by Inductively Coupled Plasma-Mass Spectrometry (ICP-MS) and found to be 295 ppm inline with the expected value.

Transmission electron microscopic images of SGP-Gold Nanoparticles confirmed the formation of gold nanoparticles with excellent resolution.

TABLE 1

Ultraviolet (UV) Spectrophotometric, Electron Microscopic, Dynamic Light Scattering and Zeta Potential Data of SGP-AuNPs and SA-AuNPs;

| Nanoparticle Sample | UV Data (nm) | Core size and Hydrodynamic Size[1] (nm) | Zeta Potential (mV) | In Vitro Stability |
|---|---|---|---|---|
| SGP- AuNP | 540 | Core Size: 30-40 nm Hydrodynamic Size: 122.5 ± 5 nm | −18 mV | Stable for over 6 months in aqueous media at physiological pH |
| Shikimic Acid functionalized AuNP SA-AuNP | 530 | 89 ± 50 nm | −16.2 mV | Stable for over 6 months in aqueous media at physiological pH |

Sizes were obtained through dynamic light scattering measurements.

The presence of presence of substantial quantities of Shikimic Acid in the aqueous extracts of Sweet gum Plant leaves was established. In addition, synthesis was demonstrated that produced well-defined gold nanoparticles through the direct interaction of shikimic acid with gold salt. The following process describes the production of gold nanoparticles using Shikimic acid (SA) as an electron donor in the process of reduction of gold salt to produce gold nanoparticles.

Production of gold nanoparticles using Shikimic acid (SA): In this process, we have demonstrated that shikimic acid, which is the main constituent in the aqueous phyto extract from Sweet gum Plant leaves, upon interaction with gold salt will produce well-defined shikimic acid functionalized gold nanoparticles. The starting compound used for the synthesis of AuNPs involved 99% pure Shikimic Acid.

Shikimic acid gold nanoparticles (SA-AuNPs) were produced by mixing of 100 mg shikimic acid (SA) and 12 mg of gum Arabic in 6 mL of doubly deionized (DI) water. The solution was stirred at 100° C. on magnetic stirrer. Generally, a temperature range of temperature range of 80-100° C. can be used. Sodium tetrachloroaurate (100 μL of 0.1 M) was added to the reaction mixture to produce gold nanoparticles (AuNPs). Change in color from yellow to burgundy wine red—indicating the characteristic Surface Plasmon Resonance (SPR) and the formation of SA-AuNPs in the homogeneous reaction mixture. Gum Arabic was used as a capping agent to render additional in vitro stability to the resulting gold nanoparticles.

The nanoparticles were characterized by various instrumentation techniques including, UV-Vis spectrophotometry, Zetasizer Nano S90, TEM and ICP-MS. The data are summarized in Table 1. Surface Plasmon Resonance (SPR) was observed at 530 nm, confirming the formation of SA-AuNPs gold nanoparticles. Formation of SK-AuNP nanoparticles was also observed through SEM imaging.

Another aspect of the invention is a process for extraction of Shikimic Acid. A related aspect is to use the extracted Shikimic Acid for the reduction of gold salts to provide gold and silver nanoparticles. A preferred Shikimic Acid extraction process uses the stems of a sweet gum plant, another process uses the leaf powder of a sweet gum plant, and another the leaves of a sweet gum plant.

Extraction of Shikimic Acid from Stems of Sweet Gum Stems: 4 gm of one cm long stems were used and boiled in 100 ml DI water for 20 minutes. The mixture was filtered to obtain the extract using Whatman Filter paper (Pore size: 8-10 microns). Filtered extracts (SG-S ext) were used for the production of Gold nanoparticles.

Extraction of Shikimic Acid from the Leaves powder of Sweet Gum Plant: 4 gm of SG leaf powder was boiled in 100 ml DI water for 20 minutes. The mixture was centrifuged to obtain the extract at 8,000 rpm for 8 minutes and then filtered using the Whatman Filter paper. This filtered extract (SG-LP ext) was used for nanoparticles preparations.

Extraction of Shikimic Acid from the Leaves of Sweet Gum Plant: 4 gm of finely cut SG leaves powder was boiled in 100 ml of DI water for 20 minutes and then filtered to obtain the extract using Whatman Filter paper. This filtered (SG-L ext) extract was used for nanoparticle preparation.

Quantification of Shikimic Acid from the above three protocols using quantitative LC-MS analysis is presented in Table 2:

| Sample preparation protocol | Extract | Analysis | Wt. of SA/ml of extract (by LCMS) |
|---|---|---|---|
| 1. Use 4 gm of one cm long stems | Use the extract (SG-S-ext) for | Estimate Shikimic | 50.9-70.1 micro gram/ml |

-continued

| Sample preparation protocol | Extract | Analysis | Wt. of SA/ml of extract (by LCMS) |
|---|---|---|---|
| and boil in 100 ml DI water for 20 minutes and then filter the extract using Filter paper. | optimizing Ag and Au nanoparticles | Acid from the extract through LCMS | |
| 2. Use 4 gm of SG Leaf Powder and boil in 100 ml DI water for 20 minutes and then filter the extract using filter paper. | Use the extract (SG-LP-ext) for optimizing Ag and Au nanoparticles | Estimate Shikimic Acid from the extract through LCMS | 175.6-290.3 micro gram/ml |
| 3. Use 4 gm of SG leaves and boil in 100 mi DI water for 20 minutes and then filter the extract using filter paper. | Use the extract (SG-L-ext) for optimizing Ag and Au nanoparticles | Estimate shikimic acid from the extract through LCMS | 176.4-213.7 micro gram/ml |

Sweet Gum Silver Nanoparticles

Sweet Gum Plant Leaves

A preferred synthetic procedure for the preparation of silver nanoparticles (GASG AgNP) also used phytochemicals from sweetgum plant with Gum Arabic as a stabilizing protein: Sweet gum leaves were washed thoroughly (2 times) with DI water to remove dust particles and cut into fine pieces. 2 mg of gum Arabic was added to 6 ml of DI water in a 20 ml vial and 250 mg of cut sweet gum leaves were added and stirred on preheated hot plate. When temperature of the solution reached 100° C., 100 micro liters of 0.1M silver nitrate solution was added. Immediately after the addition of silver salt, the color of the reaction mixture turned from colorless to dark brown, indicating the formation of nanoparticles. The reaction mixture was stirred at reduced temperature for 10 minutes before heating was turned off. The reaction mixture was stirred at room temperature (25 C) for another 60 minutes. Then the nanoparticles were analyzed by measuring the absorption coefficient using Agilent Cary 60 spectrophotometer and hydrodynamic size and zeta potential by using Malvern Z 90 zeta sizer.

Sweet Gum Extracted Phytochemicals

Production of silver nanoparticles (GASG AgNP) was conducted using phytochemicals from Sweet gum plant, pre extracted in distilled water, with Gum Arabic protein as a stabilizing agent: 4 grams of pre washed and finely cut Sweet gum leaves were boiled in 100 ml of distilled water for about 30 minutes to see transformation of the color of the mixture from pale yellow to becomes light yellow. The solution was cooled to 25° C. and then filtered to remove the leaves suspensions to obtain a clear light-yellow extract. 2 ml of this phytochemical extract was diluted with 4 ml of DI water, to which 12 mg of GA was added and subsequently heated to 100° C. Once temperature reached 100° C., the heating was turned off. To this solution, 100 micro liters of 0.1M silver nitrate solution was added. Immediately after the addition of silver salt, the color of the reaction mixture turned from light yellow to dark brown, indicating the formation.

GASG silver nanoparticles were analyzed by measuring the absorption coefficient using Agilent Cary 60 spectrophotometer and hydrodynamic size and zeta potential by using Malvern Z 90 zeta size.

TABLE 3

Characterization of GASG-Silver Nanoparticles (GASG-AgNPs).

| Silver Nanoparticle | UV Absorbance Peak (nm) | Zeta potential (mV) | Hydrodynamic size by DLS (nm) | Silver content in AgNPs (by ICP-MS, ppm) | Core size by TEM (nm) |
|---|---|---|---|---|---|
| SG-AgNP produced directly from sweet gum leaves | 415 | −22 | 185-205 | 171 | 20-30 |
| SG-AgNP produced from aqueous phytochemicals extracted from sweetgum leaves | 415 | −23.4 | 200-220 | 174 | 20-30 |

GASG-AgNPs showed UV-Visible spectra at 410 nm. hydrodynamic size of 210 nm, and zeta potential of −20 mV.

Evaluation of Viricidal Activity of University of Missouri proprietary Silver Nanoparticles (GASG AgNP) (GASG AgNP are silver nanoparticles obtained from cocktail of phytochemicals from the sweet gum plant and stabilized by Gum Arabic protein) on Human Coronavirus, Strain 229E, ATCC VR-740.

The following test parameters were employed in the Viricidal Activity (Human coronavirus, Strain 229E, ATCC VR-740) measurements:

- Test Microorganism: Human coronavirus, Strain 229E, ATCC VR-740
- Host Cell: MRC-5 (ATCC CCL-171)
- Test Substance Dilution: Ready to use liquid test substance
- Test Substance Application: 2.0 ml volume applied via pipette
- Organic Soil Load: 5% fetal bovine serum (FBS)
- Number of Replicates Per Lot: One per lot and contact time
- Contact Time(s): 1 minute and 5 minutes
- Exposure Temperature: Ambient room temperature (25.3-25.5° C.) and 38-39% Relative Humidity (RH)
- Neutralization Method(s): Sephadex LH-20 gel filtration Test Procedure.

- Stock virus was thawed and was supplemented with an organic soil load.
- Sterile glass Petri dishes (100×15 mm) were used as the test carrier. For each lot of substance and contact time assayed, one carrier was inoculated with a 0.200 ml volume of virus suspension. The appropriate number of plate recovery control carriers were also prepared.
- The inoculated carriers were dried at the appropriate temperature and relative humidity to lessen the level of virus inactivation due to drying.
- The test substance was prepared according to the Study Sponsor's instructions as requested, and a 2.0 ml volume per carrier was applied via pipette.
- The treated carriers were held for the Study Sponsor specified contact time(s) at the Study Sponsor specified exposure temperature, and then neutralized in a manner appropriate for the test substance (e.g. dilution and/or gel filtration).
- The plate recovery control carrier was held covered for the contact time then harvested and neutralized in the same manner as the test.
- Following neutralization of test and control carriers, the viral suspensions were quantified to determine the levels of infectious virus using standard cell culture techniques (e.g. TCID50).
- The inoculated cell culture plates were incubated for the period most suitable for the virus-host cell system (e.g. ~7 days).
- Following the incubation period, the assay was microscopically scored for the presence/absence of test virus and cytotoxic effects. The appropriate calculations were performed (e.g. Spearman-Karber) to determine viral titers and levels of test substance cytotoxicity, where applicable.
- The log 10 and percent reductions in viral titer were calculated for viral films exposed to the test product relative to the titer obtained for the study control carrier(s)

Success Criteria

The following measures are met to ensure the acceptability of viricidal efficacy data:

- A minimum of 4.80 log 10 to infective units/control carrier is recovered from each plate recovery control film(s).
- The virus titer control demonstrates obvious and or typical cytopathic effects on the monolayers unless a detection method other than cytopathic effect is used.
- Comparable levels of infective units must be recovered from the neutralized test substance and neutralization control substance.
- Quantification of the test and control parameters are conducted at a minimum of four determinations per dilution Calculations and Statistical Analysis:

The TCID50 (Tissue Culture Infectivity Dose) represents the endpoint dilution where 50% of the cell cultures exhibit cytopathic effects due to infection by the test virus. The endpoint dilution at which 50% of the host cell monolayers exhibit cytotoxicity is termed the Tissue Culture Dose (TCD50). The TCID50, and TCD50 was determined using the Spearman-Karber method and calculated as follows:

Negative logarithm of endpoint titer=[−Log of first dilution inoculated]−[((sum of % mortality at each dilution/100)−0.5)×Logarithm of dilution]

The result of this calculation is expressed as TCID50/0.1 ml (or volume of dilution inoculated) for the test, virus control, and neutralization control and TCD50/0.1 ml (or volume of dilution inoculated) for the cytotoxicity control.

Calculation of the Log Reduction:

The log reduction in viral titer was calculated as follows:

Plate Recovery Control Log 10 TCID50−Virus-Test Substance Log 10 TCID50

Calculation of the Percent Reduction:

The percent reduction in viral titer was calculated as follows:

$$\text{Percent Reduction}=1-(C/B)\times 100,\ \text{where:}$$

B=Average TCID50 of virus in control suspensions; C=Average TCID50 of virus in virus-test suspensions.

If multiple virus control and test replicates were performed, the average TCID50 of each parameter was calculated and the average result used to calculate the log reductions in viral titer.

TABLE 4

Virus Titer and Virus Plate Recovery Control Result

| Cell Control/Dilution | Virus Titer | Virus Plate Recovery Control |
|---|---|---|
| Cell Control | 0 0 0 0 | 0 0 0 0 |
| $10^{-1}$ | N/A | + + + + |
| $10^{-2}$ | N/A | + + + + |
| $10^{-3}$ | + + + + | + + + + |
| $10^{-4}$ | + + + + | + + + + |
| $10^{-5}$ | + + + + | + + + + |
| $10^{-6}$ | + 0 0 + | + 0 0 0 |
| $10^{-7}$ | + 0 0 0 | 0 0 0 0 |
| $10^{-8}$ | 0 0 0 0 | 0 0 0 0 |
| $TCID_{50}$ per 0.1 ml | 6.25 $Log_{10}$ | 5.75 $Log_{10}$ |
| $TCID_{50}$ per carrier | N/A | 6.05 $Log_{10}$ |

Key: + = Virus Recovered;
0 = Virus not recovered and/or no cytotoxicity observed;
T = cytotoxicity observed;
N/A = Not applicable

TABLE 5

| Test Results for GASG AgNP (42.5 ppm) | | |
|---|---|---|
| Cell Control/Dilution | Test Results 1 minute | Test Results 5 minutes |
| Cell Control | 0 0 0 0 | 0 0 0 0 |
| $10^{-1}$ | + + + + | + + + + |
| $10^{-2}$ | 0 + + + | 0 0 + + |
| $10^{-3}$ | 0 0 0 0 | 0 0 0 0 |
| $10^{-4}$ | 0 0 0 0 | 0 0 0 0 |
| $10^{-5}$ | 0 0 0 0 | 0 0 0 0 |
| $10^{-6}$ | 0 0 0 0 | 0 0 0 0 |
| $10^{-7}$ | 0 0 0 0 | 0 0 0 0 |
| $10^{-8}$ | 0 0 0 0 | 0 0 0 0 |
| $TCID_{50}$ per 0.1 ml | 2.25 $Log_{10}$ | 2.00 $Log_{10}$ |
| $TCID_{50}$ per carrier | 2.55 $Log_{10}$ | 2.30 $Log_{10}$ |
| $Log_{10}$ Reduction | 3.50 $Log_{10}$ | 3.75 $Log_{10}$ |
| Percent Reduction | 99.97% | 99.98% |

Key: + = Virus Recovered;
0 = Virus not recovered and/or no cytotoxicity observed;
T = cytotoxicity observed;
N/A = Not applicable

TABLE 6

| Test Results for GASG AgNP (10.1 ppm). | | |
|---|---|---|
| Cell Control/Dilution | Test Results 1 minute | Test Results 5 minutes |
| Cell Control | 0 0 0 0 | 0 0 0 0 |
| $10^{-1}$ | + + + + | + + + + |
| $10^{-2}$ | + + + + | + + + + |
| $10^{-3}$ | + + + + | + 0 + + |
| $10^{-4}$ | 0 + 0 0 | 0 0 0 0 |
| $10^{-5}$ | 0 0 0 0 | 0 0 0 0 |
| $10^{-6}$ | 0 0 0 0 | 0 0 0 0 |
| $10^{-7}$ | 0 0 0 0 | 0 0 0 0 |
| $10^{-8}$ | 0 0 0 0 | 0 0 0 0 |
| $TCID_{50}$ per 0.1 ml | 3.75 $Log_{10}$ | 3.25 $Log_{10}$ |
| $TCID_{50}$ per carrier | 4.05 $Log_{10}$ | 3.55 $Log_{10}$ |
| $Log_{10}$ Reduction | 2.00 $Log_{10}$ | 2.50 $Log_{10}$ |
| Percent Reduction | 99.0% | 99.68% |

Key: + = Virus Recovered;
0 = Virus not recovered and/or no cytotoxicity observed;
T = cytotoxicity observed;
N/A = Not applicable

TABLE 7

| Cytotoxicity Control Results | | |
|---|---|---|
| Cell Control/ Dilution | Cytotoxicity Control GASG AgNP (42.5 ppm) | Cytotoxicity Control GASG AgNP (10.1 ppm) |
| Cell Control | 0 0 0 0 | 0 0 0 0 |
| $10^{-1}$ | 0 0 0 0 | 0 0 0 0 |
| $10^{-2}$ | 0 0 0 0 | 0 0 0 0 |
| $10^{-3}$ | 0 0 0 0 | 0 0 0 0 |
| $TCID_{50}$ per 0.1 ml | ≤0.50 $Log_{10}$ | ≤0.50 $Log_{10}$ |

Key: + = Virus Recovered;
0 = Virus not recovered and/or no cytotoxicity observed;
T = cytotoxicity observed;
N/A = Not applicable

TABLE 8

| Neutralization Control Results | | | |
|---|---|---|---|
| Cell Control/Dilution | Control Substance | Neutralization Control GASG AgNP (42.5 ppm) | Neutralization Control GASG AgNP (10.1 ppm) |
| Cell Control | 0 0 0 0 | 0 0 0 0 | 0 0 0 0 |
| $10^{-1}$ | + + + + | + + + + | + + + + |
| $10^{-2}$ | + + + + | + 0 + 0 | 0 |
| $10^{-3}$ | + 0 + 0 | 0 0 0 0 | 0 |
| $10^{-4}$ | 0 0 0 0 | 0 0 0 0 | 0 |
| $10^{-5}$ | 0 0 0 0 | 0 0 0 0 | 0 |
| $10^{-6}$ | 0 0 0 0 | 0 0 0 0 | 0 |
| $TCID_{50}$ per 0.1 ml | 3.00 $Log_{10}$ | 2.00 $Log_{10}$ | 1.75 $Log_{10}$ |

Key: + = Virus Recovered;
0 = Virus not recovered and/or no cytotoxicity observed;
T = cytotoxicity observed;
N/A = Not applicable The test substance and control substance demonstrated comparable levels of infective units recovered in the Neutralization Control.

Investigations evaluating efficacy of GASG AgNP to neutralize VSV-pseudotype SARS-COV-2 Virus.

Study Design

Six Test Articles (TA) provided by the client were evaluated for neutralizing activity ($ID_{50}$) against IBT's VSV-pseudotype neutralization assay for SARS-COV-2, VSV-based pseudovirus expressing SARS-COV-2 in Vero cells. Cytotoxicity was assessed first and starting dilutions were updated for the neutralization assay.

Neutralization Assay Description

The vesicular stomatitis virus (rVSV) whose glycoprotein gene (G) has been deleted is used as the base platform for IBT's pseudotype-based neutralization assay. The VSV-G glycoprotein is transiently expressed by transfection to produce virus particles. To create pseudotyped viruses, the VSV-G is substituted with SARS-COV-2 Spike protein (Full length Spike protein lacking terminal eighteen amino acids of the cytoplasmic domain). The system has been developed and the resulting virus—rVSV-ΔG SARS-CoV-2 S—can be handled at Biosafety Level 2 (BSL-2). rVSV-ΔG SARS-CoV-2 S is cytopathic and expresses firefly luciferase. Infection efficiency can be measured by quantification of luciferase activity reading the relative light units (RLU) on a luminometer.

Briefly, rVSV-ΔG SARS-COV-2 S is pre-incubated with and without the Test Article (TA) as well as IBT's internal assay control for 1-hour. A monolayer of Vero cells is then infected with the virus alone and with the virus/TA mixtures in triplicate and incubated for 24-hours at 37° C.; a minimum of six virus only and cells only wells are always included. Firefly luciferase activity is then measured in all the wells and neutralization titers of each TA is calculated by comparing the RLU values of antibody treated versus the virus and cells only control. Neutralization titers [$_{50}$% inhibitory dose ($ID_{50}$)] are defined as the reciprocal of the serologic reagent dilution (or concentration for purified reagents) that caused a 50% reduction in RLUs compared to virus control wells.

TABLE 9

Test articles

| Name | Molecular Weight | Diluent | Stock Concentration | Start Concentration $CC_{50}$ | Start Concentration $ID_{50}$ | Dilution Factor |
|---|---|---|---|---|---|---|
| GASG AgNP | N/A | Medium | 170 ppm | 42.5 ppm | 15 ppm | 2 |
| GA (control) | N/A | Medium | 2 mg/mL | 0.5 mg/mL | 0.5 mg/mL | 2 |

TABLE 10

Viruses used as challenge

| Virus | | Lot# | Stock dilution | RLU/well | Incubation time | Cell line |
|---|---|---|---|---|---|---|
| rVSV-DG CoV-2 S | SARS- | 06182020c | 1:20 | 15,000 | 1 day | Vero |

TABLE 11

Cell lines.

| Cell Line | Origin | Cat# | Passage | Seeding density |
|---|---|---|---|---|
| [2]Vero | ATCC | CCL-81 | 20 | 6.00E+04 cells/well |

[2]African green monkey kidney cells

TABLE 12

Reagents and consumables.

| Item | Vendor | Cat#/Model | Notes |
|---|---|---|---|
| T225 flasks | Corning | N/A | |
| 96-well Flat Clear Bottom Black TC-treated Microplate, Sterile | Corning | 3603 | |
| Minimum Essential Medium (EMEM) | GIBCO | 10370 | |
| 0.25% Trypsin EDTA | GIBCO | 2500-056 | |
| Heat-inactivated Fetal Bovine Serum (HI-FBS) | GIBCO | 16140-071 | 10% in Medium |
| Penicillin-Streptomycin(P/S) (10,000U/mL) | GIBCO | 15140-122 | 100x dilution in medium to 100 units/mL for culture media |
| 1X DPBS | Corning | 21-031-CM | |
| L-Glutamine (200 mM) | GIBCO | 25030-81 | 100x dilution in medium to 2 mM final |
| CellTiter-Glo ® Luminescent Cell Viability Assay | Promega | G7573 | |
| Bright-Glo ™ Luciferase Assay System | Promega | E2610 | Reconstituted and kept frozen at −80° C. in 10 ml aliquots |

TABLE 13

| Equipment and Software | | |
|---|---|---|
| Item | Vendor | Cat#/Model |
| Luminescence plate reader | BioTek Instruments | Cytation ™ 5 |
| Microsoft Office | Microsoft | Office 365 |
| XLfit | IDBS | 5.4 |

TABLE 14

| Working Reagent | | |
|---|---|---|
| Reagent | Base Medium | Additives |
| Growth medium | MEM | 10% HI-FBS, 1x P/S, 2 mM L-Gln |
| Infection medium | MEM | 1% HI-FBS, 1x P/S, 2 mM L-Gln |

Cytotoxicity

Cell Seeding 60,000 Vero cells were seeded (Table 11) in 96-well flat bottom black cell culture plates in 10% serum medium (Table 12), and incubated overnight.

Test Article Dilution and Cell Incubation.

Eight 2-fold serial dilutions of each TAs (Table 9) were prepared in 1% serum medium at two times (2×) the final intended concentration. All medium was removed from the 96-well black plates and 100 μl of each TA dilutions were added in triplicate to the Vero cells; cells only received infection medium only. Plates were incubated for 1-hour, 100 μl of infection medium was then added and the cells were incubated at 37° C. and 5% $CO_2$ for 24-hours.

Firefly Luciferase Readout.

200 μl of medium was removed from the black plates and 100 μl of CellTiter-Glo® reagent was prepared and added to each well as instructed by the manufacturer. Plates were read immediately in the CYTATION™ 5 (Cell Imaging Multi-mode Reader) for firefly luciferase activity and the relative light unit (RLU) were collected.

Neutralization Assay.

Cell Seeding 60,000 Vero cells were seeded (Table 11) in 96-well flat bottom black cell culture plates in 10% serum medium (Table 12), and incubated overnight.

Test Article Dilution.

Seven 2-fold dilutions of TAs (Table 9) were prepared in 1% serum medium at two times (2×) the final intended concentration. Starting concentrations were changed by the Client after reviewing the $CC_{50}$ data.

Virus Dilution and TA/Virus Mix Pre-Incubation.

rVSV-SARS-COV-2 S (Table 10) was diluted 1:10 in 1% serum medium to obtain a final dilution of 1:20 in 2.5 mL. 175 μl of virus inoculum was then mixed with 175 μl of each TA concentrations for 350 μl final; 350 μl of virus only (VO) was also prepared. All mixtures were incubated for 1-hour at 37° C. and 5% $CO_2$.

Vero Cells Infection.

All medium was removed from the 96-well black plates and 100 μl of each virus/TA mixtures were added in triplicate to the Vero cells; 100 μl of virus only and 100 μl of 1% serum medium were also added in a minimum of 6 wells, respectively and incubated for 24-hours at 37° C. and 5% $CO_2$.

Firefly Luciferase Readout.

100 μl of BRIGHT-GLO™ reagent (Luciferase Assay System) was added to each well as instructed by the manufacturer. Plates were read immediately in our luminometer and the relative light unit (RLU) was measured.

Data Evaluation.

Data were imported into Excel to calculate $ID_{50}$ values. The XLfit 5 plug-in was used with fit #205.

Data Summary

TABLE 15

| Summary of Antiviral Efficacy of the Test Article. | | |
|---|---|---|
| TA | $CC_{50}$ | $ID_{50}$ |
| GASG AgNP | 15.50 | 2.577 |
| GA (control) | ND | ND |

Results.

The study demonstrated the viricidal efficacy of the present silver nanoparticle samples: SG AgNP (42.5 ppm) and SG AgNP (10.1 ppm) (both produced using cocktails of sweet gum plant) against the Human coronavirus Strain 229E, supplemented with a 5% FBS organic soil load, at contact times of 1 minute and 5 minutes at room temperature (25.3-25.5° C. and 38-39% RH). The Plate Recovery Control demonstrated a viral titer of 5.75 Log 10 TCID50 per 0.1 ml and 6.05 Log 10 TCID50 per carrier.

The evaluated test substance, GASG AgNP (42.5 ppm) demonstrated a 3.50 Log 10 reduction in viral titer (99.97%) at a contact time of 1 minute and a 3.75 Log 10 reduction in viral titer (99.98%) at a contact time of 5 minutes, as compared to the titer of the corresponding Plate Recovery Control.

The evaluated test substance, GASG AgNP (10.1 ppm) demonstrated a 2.00 Log 10 reduction in viral titer (99.0%) at a contact time of 1 minute and a 2.50 Log 10 reduction in viral titer (99.68%) at a contact time of 5 minutes, as compared to the titer of the corresponding Plate Recovery Control.

It is important to recognize that no test substance cytotoxicity was detected in the lots of test substance assayed (≤0.50 Log 10). It is noteworthy that the test substance and control substance demonstrated comparable levels of infective units recovered in the Neutralization Control.

The U.S. EPA requires a ≥3 log 10 reduction in viral titer as compared to the corresponding plate recovery control. Therefore, in this context, the evaluated proprietary antiviral/antibacterial agent: GASG AgNP (at 42.5 ppm) demonstrated a 3.50 Log 10 reduction in viral titer (99.97%) at a contact time of 1 minute and a corresponding 3.75 Log 10 reduction in viral titer (99.98%) at a contact time of 5 minutes, as compared to the titer of the corresponding Plate Recovery Control. These data demonstrate effectiveness to be used in antiviral/antibacterial disinfectant products including antiviral/antibacterial disinfectant sprays and large area disinfectant products for household, commercial establishments, aviation industry, health care industry and allied human dwelling applications. Vero cells seeded in 96-well plates were incubated with serial dilutions of TA only for cytotoxicity ($CC_{50}$; in blue) and with rVSV-SARS-COV-2 S ($ID_{50}$; in green). Values were calculated using XLfit model 205 using the average values of triplicates for each experiment. The concentration of GASG-AgNP at which this agent is highly effective in neutralizing the rVSV-SARS-COV-2 S virus is significantly lower than the toxicity limits of this agent as measured using Vero cells.

SA-AuNP and SGP-AuNPs testing against various cancer cell lines.

Cell lines and protocol. Human prostate cancer (PC-3), breast cancer (MDA-MB-231), and pancreatic cancer (PANC-1) cells were obtained from the American Type Culture Collection (ATCC; Manassas, VA), and cultured by the University of Missouri Cell and Immunobiology Core facility using procedures recommended by ATCC.

Cell viability assay. The effect of SA-AuNPs and SGP-AuNPs with higher corona on PC-3, MDA-MBA-231, and PANC-1 cell viability was determined using MTT assay (Sigma, St. Louis, USA). The intensity of the developed color was measured by micro plate reader (Molecular device, USA) operating at 570 nm wavelength. Percent cell viability was calculated by using the formula: (T/C)×100, where C=Absorbance of control, T=Absorbance of treatment. The IC-50 values were calculated using the Origin software.

Therapeutic agents: SA-AuNP and SGP-AuNPs were produced at Institute of Green Nanotechnology, University of Missouri, Columbia-MO-USA; and it was used without any modification.

Cell viability profile of SA-AuNP and SGP-AuNPs: Serial dilutions were prepared in RPMI/DMEM media to treat PC-3, MDA-MB-231, and PANC-1 cell lines. The cell viability profile of SA-AuNP and SGP-AuNPs were evaluated against cancer cells by MTT assay. The cell viability profiles demonstrated that SA-AuNP and SGP-AuNPs exhibited dose dependent efficacy in the death of cancer cells.

The testing demonstrated increasing reduction in cancer cell viability with increasing concentration of both SA-AuNP and SGP-AuNPs over a period of 48 and 72 hours. Each concentration from 10-22.4 μg/mL reduced cell viability compared to a control untreated, and significant reduction was demonstrated at concentrations 100 and 200 μg/ml. Therefore, SA-AuNP and SGP-AuNPs are excellent cancer therapeutic agents either on their own or in adjuvant combinations with chemotherapy or radiation therapy.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A nanomaterial comprising a gold nanoparticle or silver nanoparticle having a nanoparticle surface that consists of shikimic acid-3,4,5-trihydroxy-1-cyclohexene-1-carboxylic acid having the structure of:

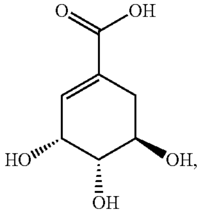 [SMILES: O=C(O)C1=C[C@@H](O)[C@@H](O)[C@H](O)C1]

wherein the particle has a core size of 30-40 nm.

2. The nanomaterial of claim 1, wherein the particle with the surface has a size of 89±50 nm.

3. The nanomaterial of claim 1 wherein the particle is a gold nanoparticle and has a hydrodynamic size of 122.5±5 nm.

4. The nanomaterial of claim 1, wherein the particle is a silver nanoparticle and has a hydrodynamic size of 185-205 nm.

5. A nanomaterial comprising a silver nanoparticle having a nanoparticle surface that consists of shikimic acid-3,4,5-trihydroxy-1-cyclohexene-1-carboxylic acid having the structure of:

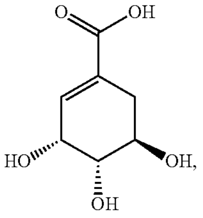 [SMILES: O=C(O)C1=C[C@@H](O)[C@@H](O)[C@H](O)C1]

wherein the particle has a hydrodynamic size of 185-205 nm.

6. The nanomaterial of claim 1, wherein the particle is a silver nanoparticle and has a hydrodynamic size of 200-220 nm.

7. A method for synthesizing a nanomaterial, the method comprising obtaining a phytoextract solution from sweet gum plant leaves, sweet gum stems or powder of a sweet gum plant, filtering the solution and reacting the solution with gold or silver salts to produce the nanomaterial, wherein the phytoextract comprises isolated Shikimic Acid, and the method comprises a preliminary step of extracting Shikimic Acid by boiling one of stems of a sweet gum plant, leaf powder of a sweet gum plant, and the leaves of a sweet gum plant in DI water for a predetermined period and filtering the solution after boiling to obtain Shikimic Acid extract.

8. The method of claim 7, wherein the obtaining comprises washing the sweet gum plant leaves to remove dust particles, cutting the sweet gum plant leaves into pieces; adding gum Arabic to distilled water; and adding the pieces to the distilled water; and the reacting comprises heating and stirring the distilled water with the pieces to a temperature of at least 100° C., then adding the gold or silver salts and stirring for a period of time until nanoparticle formation occurs.

9. The method of claim 7, wherein the reacting is conducted in a temperature range of 60° C.-100° C.

10. The method of claim 9, wherein the reacting is conducted with Gum Arabic.

11. An antiviral/antibacterial agent comprising sweet gum mediated silver nanoparticles having a core size and in a concentration having efficacy as an antiviral/antibacterial exceeding a 3 log 10 reduction in viral titer, in an oral consumption carrier for use as a pharmaceutical to treat viruses.

* * * * *